United States Patent
Chen et al.

(10) Patent No.: US 8,420,672 B2
(45) Date of Patent: Apr. 16, 2013

(54) SOLID FORMS OF 3-(4-AMINO-1-OXO-1,3-DIHYDRO-ISOINDO1-2-YL)-PIPERIDINE-2,6-DIONE AND METHODS OF MAKING THE SAME

(75) Inventors: Chen-Tung Chen, Shan-Hua (TW); Inze Lin, Shan-Hua (TW)

(73) Assignee: ScinoPharm Taiwan Ltd., Tainan (TW)

( * ) Notice: Subject to any disclaimer, the term of this patent is extended or adjusted under 35 U.S.C. 154(b) by 116 days.

(21) Appl. No.: 12/885,065

(22) Filed: Sep. 17, 2010

(65) Prior Publication Data

US 2011/0065750 A1 Mar. 17, 2011

Related U.S. Application Data

(60) Provisional application No. 61/243,204, filed on Sep. 17, 2009.

(51) Int. Cl.
*A61K 31/454* (2006.01)
*C07D 401/04* (2006.01)

(52) U.S. Cl.
USPC .......................................... 514/323; 546/201

(58) Field of Classification Search .................. 514/323; 546/201
See application file for complete search history.

(56) References Cited

U.S. PATENT DOCUMENTS

| 7,465,800 B2 | 12/2008 | Jaworsky et al. |
| 2006/0160854 A1 | 7/2006 | Muller et al. |
| 2009/0149500 A1 | 6/2009 | Jaworski et al. |
| 2009/0187023 A1 | 7/2009 | Jaworsky et al. |

FOREIGN PATENT DOCUMENTS

| WO | WO2005/023192 | 3/2005 |
| WO | WO2006/028964 | 3/2006 |
| WO | WO2009/114601 | 9/2009 |
| WO | WO2010/054833 | 5/2010 |
| WO | WO2010/1000476 | 9/2010 |

OTHER PUBLICATIONS

Kirk-Othmer "Crystallization" Encyclopedia of chem. Tech. v.8, p. 95-147 (2004).*
Davidovich et al. "Detection of polymorphism . . . " Am. Pharm. Review, v. 7(1), p. 10, 12, 14, 16, 100 (2004).*
Vippagunta et al. "Crystal solids" adv. drug. del. rev. v.48, 3-26 (2001).*
Byrn et al. "Solid-state Chemistry of drugs" p. 63, (1999).*
Ohannesian et al. "Handbook of pharmaceutical analysis" p. 8-9 (2002).*

* cited by examiner

*Primary Examiner* — Celia Chang
(74) *Attorney, Agent, or Firm* — Enshan Hong; Kent H. Cheng; VLP Law Group LLP

(57) ABSTRACT

The present invention provides for new crystalline and amorphous forms of 3-(4-amino-1-oxo-1,3-dihydro-isoindol-2-yl)-piperidine-2,6-dione, and methods of making the same.

7 Claims, 10 Drawing Sheets

| Caption Legend | Angle 2-Theta ° | d value Angstrom | Intensity Cps | Intensity % |
|---|---|---|---|---|
| d=39.46058 | 2.237 | 39.46058 | 21.4 | 23.3 |
| d=13.34515 | 6.618 | 13.34515 | 11.6 | 12.6 |
| d=11.53274 | 7.660 | 11.53274 | 15.1 | 16.5 |
| d=11.19127 | 7.894 | 11.19127 | 13.1 | 14.3 |
| d=10.25295 | 8.617 | 10.25295 | 9.62 | 10.5 |
| d=7.76940 | 11.380 | 7.76940 | 14.6 | 15.9 |
| d=7.32580 | 12.071 | 7.32580 | 91.6 | 100.0 |
| d=7.03358 | 12.575 | 7.03358 | 79.3 | 86.6 |
| d=6.60599 | 13.393 | 6.60599 | 67.5 | 73.7 |
| d=6.47020 | 13.675 | 6.47020 | 35.1 | 38.4 |
| d=6.36048 | 13.912 | 6.36048 | 25.5 | 27.8 |
| d=6.26620 | 14.122 | 6.26620 | 22.2 | 24.2 |
| d=5.80996 | 15.238 | 5.80996 | 33.5 | 36.5 |
| d=5.60032 | 15.812 | 5.60032 | 43.6 | 47.6 |
| d=5.38052 | 16.462 | 5.38052 | 17.8 | 19.4 |
| d=5.16325 | 17.160 | 5.16325 | 15.1 | 16.5 |
| d=4.90731 | 18.062 | 4.90731 | 26.7 | 29.1 |
| d=4.69652 | 18.880 | 4.69652 | 49.7 | 54.3 |
| d=4.63164 | 19.147 | 4.63164 | 27.8 | 30.4 |
| d=4.53308 | 19.567 | 4.53308 | 21.1 | 23.1 |
| d=4.43302 | 20.013 | 4.43302 | 30.9 | 33.8 |
| d=4.29894 | 20.644 | 4.29894 | 19.8 | 21.6 |
| d=4.24591 | 20.905 | 4.24591 | 17.3 | 18.9 |
| d=4.15944 | 21.345 | 4.15944 | 18.0 | 19.7 |
| d=4.01792 | 22.106 | 4.01792 | 49.0 | 53.6 |
| d=3.93608 | 22.571 | 3.93608 | 38.0 | 41.5 |
| d=3.87622 | 22.925 | 3.87622 | 18.6 | 20.3 |
| d=3.84107 | 23.137 | 3.84107 | 16.2 | 17.7 |
| d=3.72410 | 23.875 | 3.72410 | 69.4 | 75.7 |
| d=3.60019 | 24.709 | 3.60019 | 41.2 | 45.0 |
| d=3.45506 | 25.765 | 3.45506 | 70.9 | 77.5 |
| d=3.34410 | 26.635 | 3.34410 | 33.1 | 36.1 |
| d=3.23681 | 27.535 | 3.23681 | 31.0 | 33.9 |
| d=3.12106 | 28.577 | 3.12106 | 16.5 | 18.1 |
| d=3.05380 | 29.221 | 3.05380 | 19.6 | 21.5 |
| d=2.93542 | 30.427 | 2.93542 | 16.5 | 18.1 |
| d=2.91551 | 30.640 | 2.91551 | 17.9 | 19.6 |
| d=2.87293 | 31.105 | 2.87293 | 13.9 | 15.1 |
| d=2.79540 | 31.991 | 2.79540 | 12.8 | 14.0 |
| d=2.69856 | 33.171 | 2.69856 | 11.2 | 12.2 |
| d=2.64118 | 33.914 | 2.64118 | 11.5 | 12.6 |
| d=2.63596 | 33.983 | 2.63596 | 12.1 | 13.2 |
| d=2.59989 | 34.469 | 2.59989 | 20.0 | 21.9 |
| d=2.51215 | 35.713 | 2.51215 | 8.77 | 9.6 |
| d=2.45365 | 36.594 | 2.45365 | 8.81 | 9.6 |
| d=2.38191 | 37.737 | 2.38191 | 8.85 | 9.7 |
| d=2.34468 | 38.359 | 2.34468 | 9.38 | 10.2 |
| d=2.30298 | 39.082 | 2.30298 | 8.70 | 9.5 |
| d=2.28742 | 39.359 | 2.28742 | 7.58 | 8.3 |

FIND PEAKS:
  Spectrum:
  Region: 4000.00    400.00
  Absolute threshold:    72.536
  Sensitivity: 50
  Peak list:
    Position: 1707.66    Intensity: 48.316
    Position: 420.61     Intensity: 56.166
    Position: 1206.38    Intensity: 56.354
    Position: 1492.56    Intensity: 58.190
    Position: 748.24     Intensity: 59.617
    Position: 1609.00    Intensity: 60.464
    Position: 1348.38    Intensity: 60.631
    Position: 1237.98    Intensity: 61.005
    Position: 468.48     Intensity: 62.033
    Position: 431.33     Intensity: 61.324
    Position: 1298.92    Intensity: 65.018
    Position: 406.08     Intensity: 65.395
    Position: 1420.81    Intensity: 67.564
    Position: 607.89     Intensity: 68.699
    Position: 1265.84    Intensity: 69.188
    Position: 1463.15    Intensity: 69.673
    Position: 1450.48    Intensity: 69.702
    Position: 460.85     Intensity: 70.072
    Position: 807.42     Intensity: 70.383
    Position: 555.02     Intensity: 71.074
    Position: 3240.62    Intensity: 71.561
    Position: 455.53     Intensity: 71.876

SOLID FORMS OF 3-(4-AMINO-1-OXO-1,3-DIHYDRO-ISOINDO1-2-YL)-PIPERIDINE-2,6-DIONE AND METHODS OF MAKING THE SAME

RELATED APPLICATIONS

This application claims priority from U.S. Provisional Patent Application Ser. No. 61/243,204, which was filed on Sep. 17, 2009. The entire content of this provisional application is incorporated herein as reference.

BACKGROUND OF THE INVENTION

Field of Invention

The present invention is concerned with quarter hydrate crystalline form or amorphous form of 3-(4-amino- 1-oxo-1,3-dihydro-isoindol-2-yl)-piperidine-2,6-dione and process for their preparation, pharmaceutical compositions containing the novel forms.

SUMMARY OF THE INVENTION 3-(4-amino-1-oxo-1,3-dihydro-Isoindol-2-yl)-piperidine-2,6-dione or lenalidomide is known to be useful in treating and preventing various diseases, including, but not limited to, inflammatory diseases, autoimmune diseases, and cancer.

We have obtained crystalline and amorphous forms of 3-(4-amino-1-oxo-1,3-dihydro -Isoindol-2-yl)-piperidine-2,6-dione that exhibit unique properties.

Synthesis of Crystalline Form I, Quarterhydrate (1:0.25)

Preparation of 3-(4-amino-1-oxo-1,3-dihydro-isoindol-2-yl)-piperidine-2,6-dione Form I, quarterhydrate (1:0.25)

Form I can be generally obtained by evaporation in a methanol/water solvent system. Form I can also be obtained from Form A in a hot water slurry system. Form A is an anhydrous form disclosed in U.S. Pat. No. 7,465,800. Specific examples of both methods are shown below.

EXAMPLE 1

A mixture of Form A 3-(4-amino-1-oxo-1,3-dihydro-Isoindol-2-yl)-piperidine-2,6-dione (300 mg) and aqueous solution (30 ml) was heated for 3 hours at 60° C. The mixture was filtered and the wet cake was dried for about 28 hours at 40° C. under reduced pressure. The solid was analyzed by XRD and IR and identified as form I.

EXAMPLE 2

A 500 ml jacket reactor was charged with a solution of 3-(4-amino-1-oxo-1,3 dihydro-isoindol-2-yl)-piperidine-2,6-dione (about 1.3 g) and methanol (about 260 ml). The solution was heated to 60° C. The solution was concentrated to remove around ⅔ of methanol and the slurry solution was charged with water (about 300 ml). The mixture was further concentrated to remove methanol. The resulting slurry was filtered and the wet cake was dried at 40° C. under reduced pressure for around 35 hours. The dried sample was submitted for XRPD, TGA, DSC and infrared diffuse reflectance analysis. The results of the analysis are shown in FIGS. 1-4.

Preparation of the amorphous form of 3-(4-amino-1-oxo-1,3-dihydro-isoindol-2-yl)-piperidine-2,6-dione

EXAMPLE 3

Crystalline 3-(4-amino-1-oxo-1,3-dihydro-isoindol-2-yl)-piperidine-2,6-dione (about 300 mg) was dissolved in methanol (50 ml) at 60° C. to obtain a clear solution. The solution was concentrated under reduced pressure to remove methanol and solid was obtained. The solid substance was analyzed by XRD and infrared diffuse reflectance analysis, and identified as an amorphous form. See FIGS. 5-6a-c.

BRIEF DESCRIPTION OF THE DRAWINGS

In the drawings:

FIG. 1a-b is a characteristic X-ray powder diffraction pattern of Form I, quarterhydrate;

FIG. 6a-c is an infrared diffuse-reflectance pattern of amorphous form.

Figure 1A:
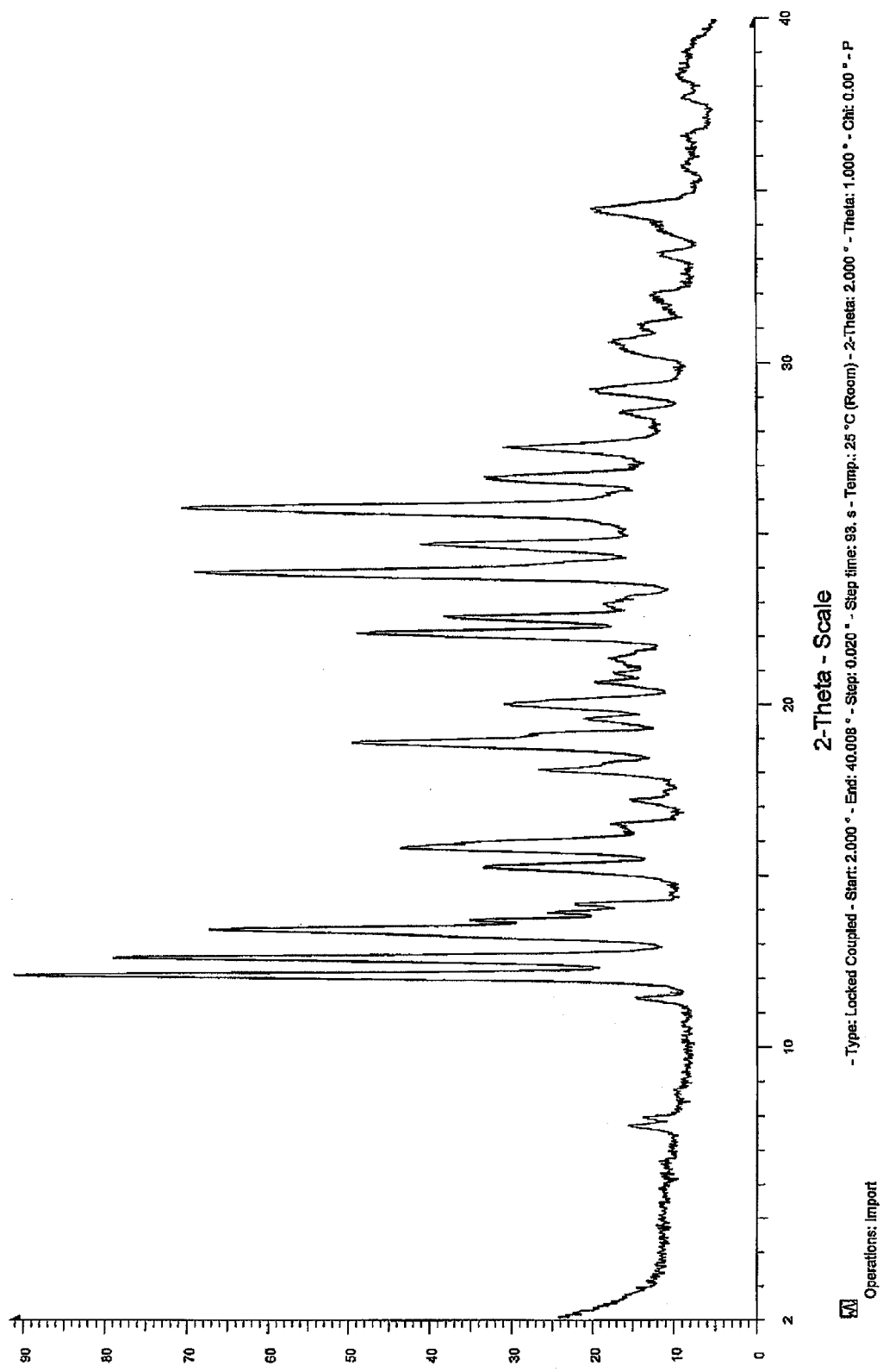
Figure 2:
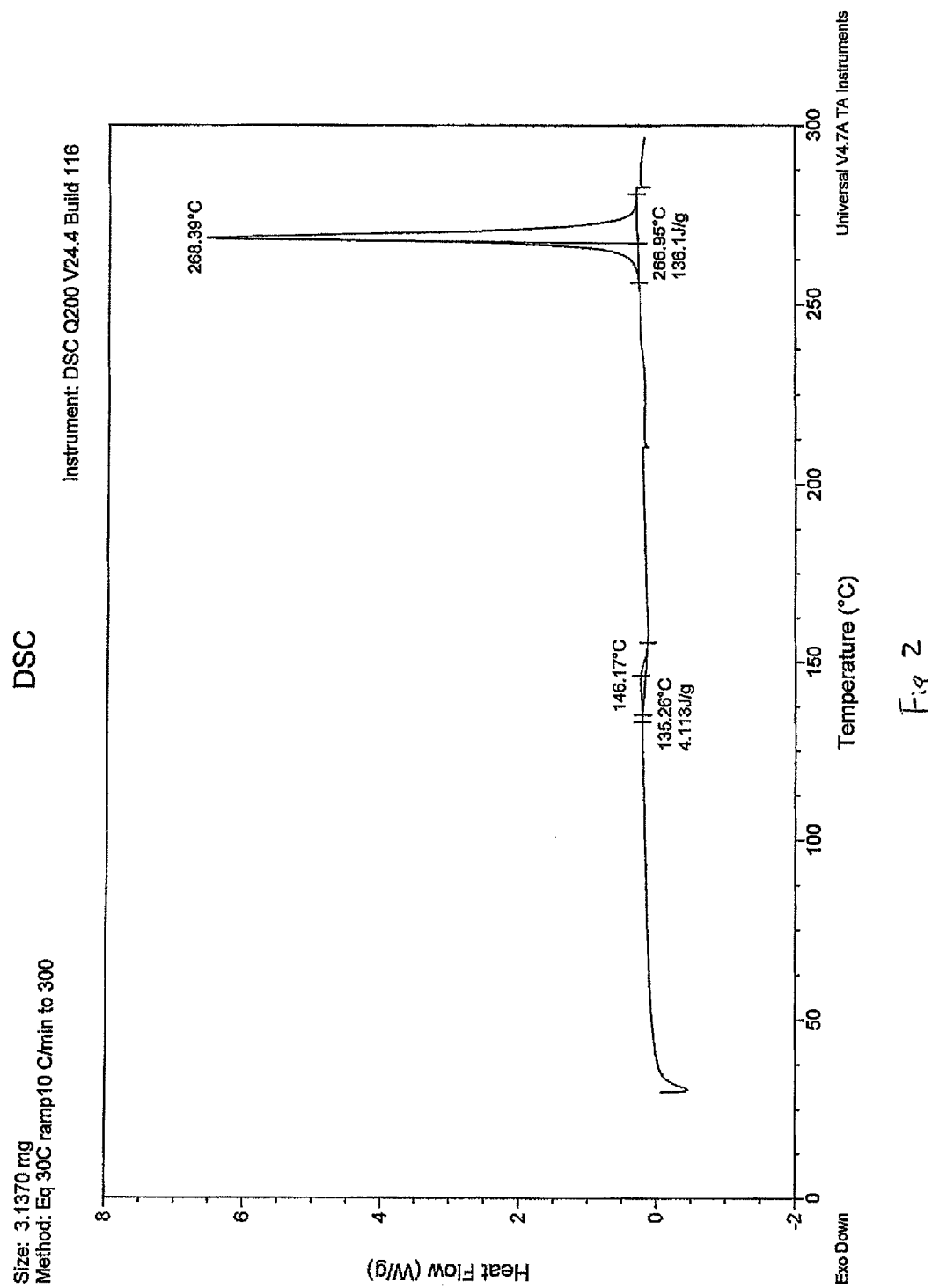
FIG. 2 is the Differential Scanning calorimetry Pattern of Form I, quarterhydrate.
Figure 3:
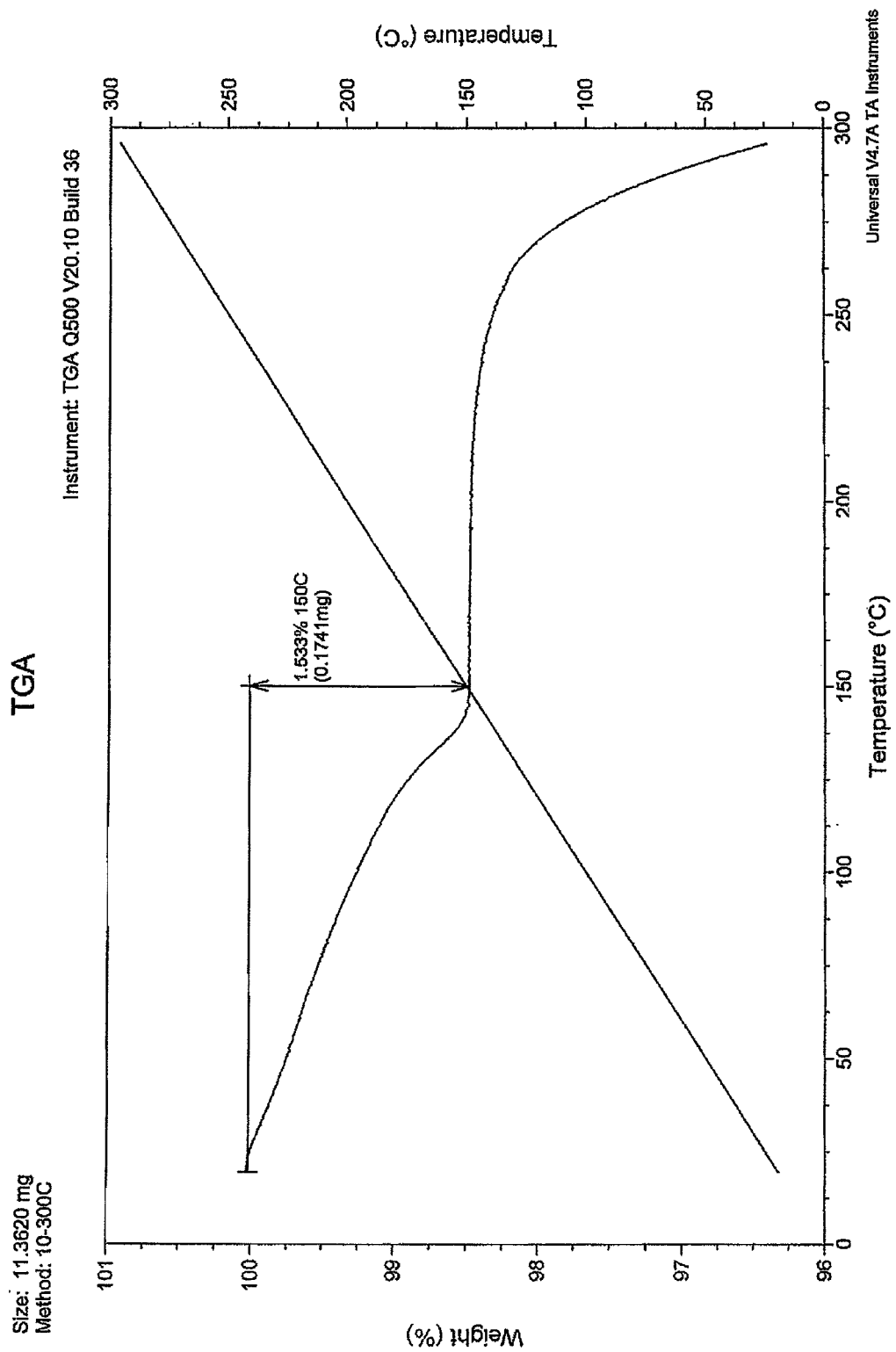
FIG. 3 is the Thermogravimetric Analysis Pattern of Form I, quarterhydrate.

We claim:

1. A crystalline form of 3-(4-amino-1-oxo-1,3-dihydro-isoindol-1-2-yl)-piperidine-2,6-dione quarterhydrate (1:0.25) having an X-ray powder diffraction pattern substantially in accordance with that shown in FIG. 1a-b; and having a TGA pattern as substantially shown in FIG. 3.

2. The crystalline form of claim 1 having an infrared diffuse-reflectance pattern with peaks at approximately 1698, 1662, 1493, 1350 and 1203 wavenumbers.

Figure 4A:
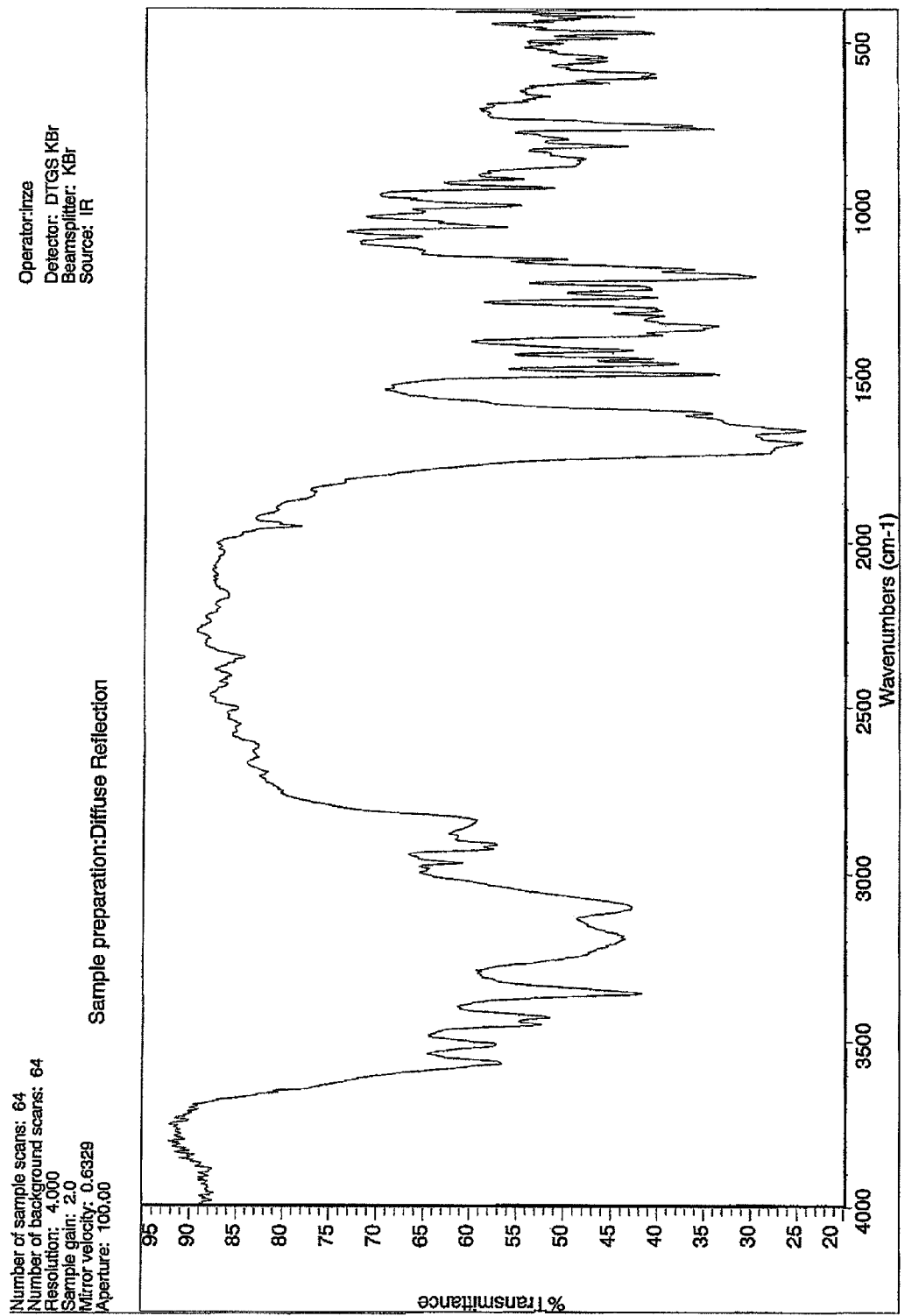
FIG. 4 a-b is an infrared diffuse-reflectance pattern of Form I, quarterhydrate.
Figure 4:
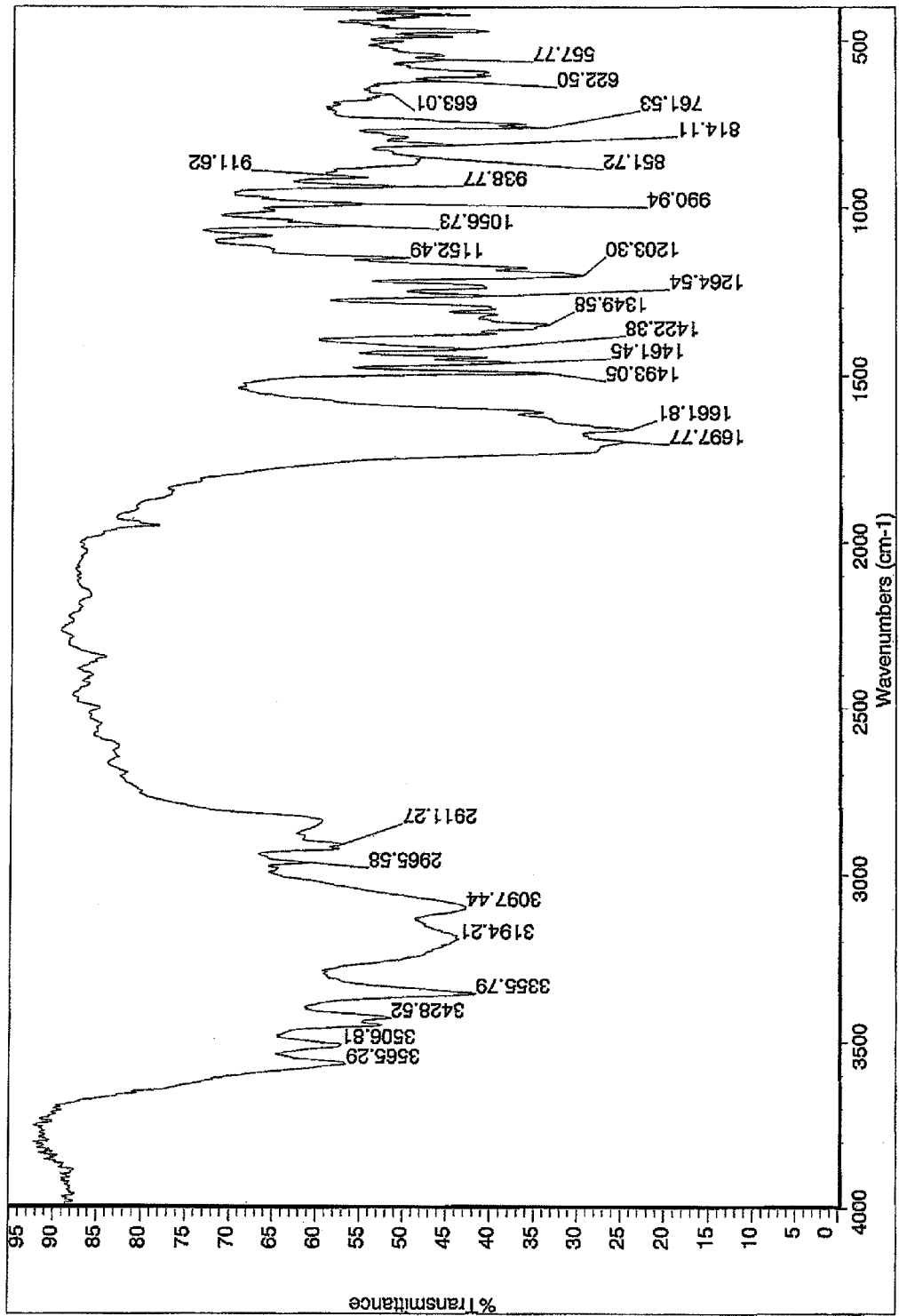
Figure 5:
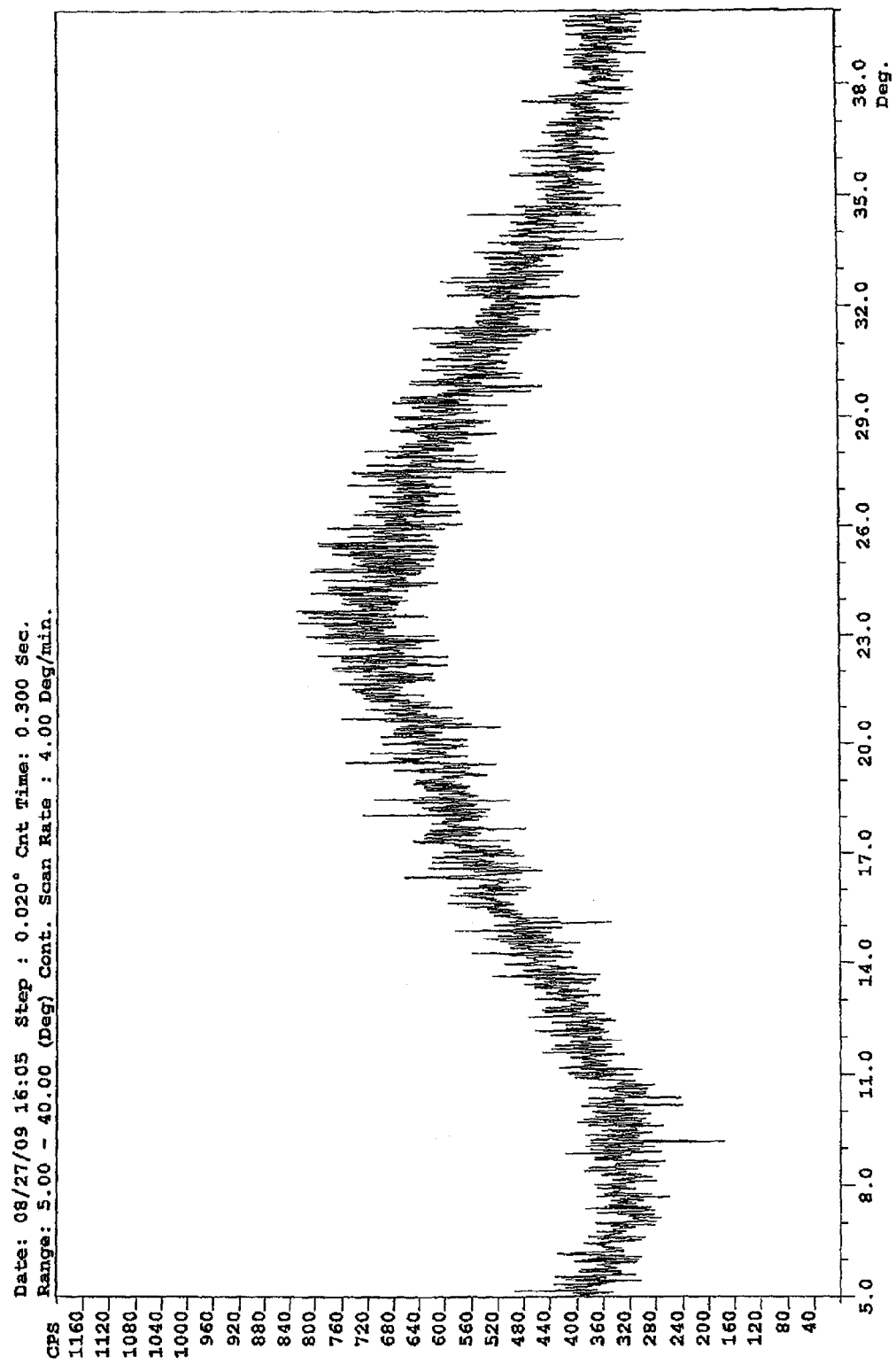
FIG. 5 is a characteristic X-ray powder diffraction pattern of the amorphous form.
Figure 6A:
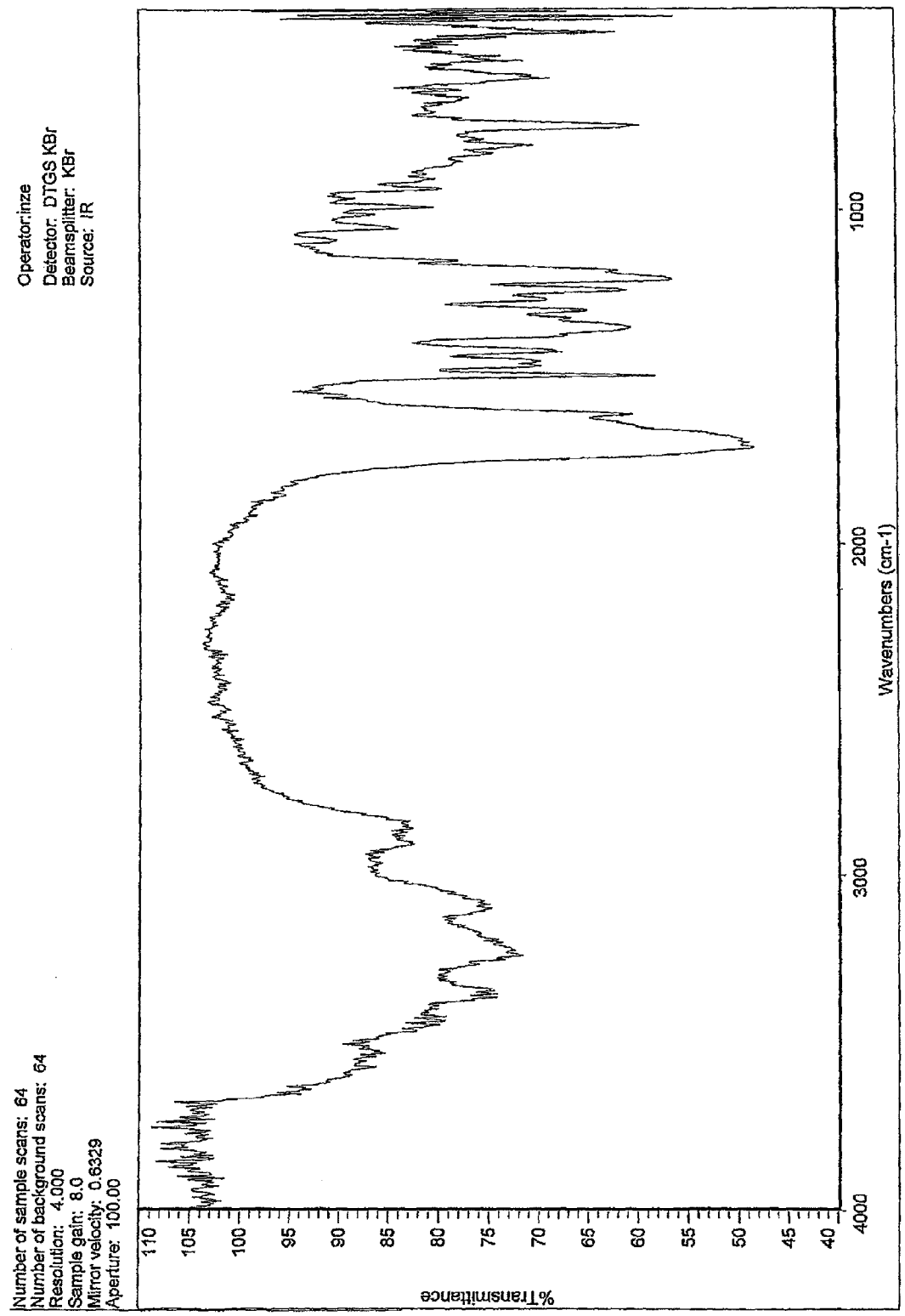
Figure 6B:
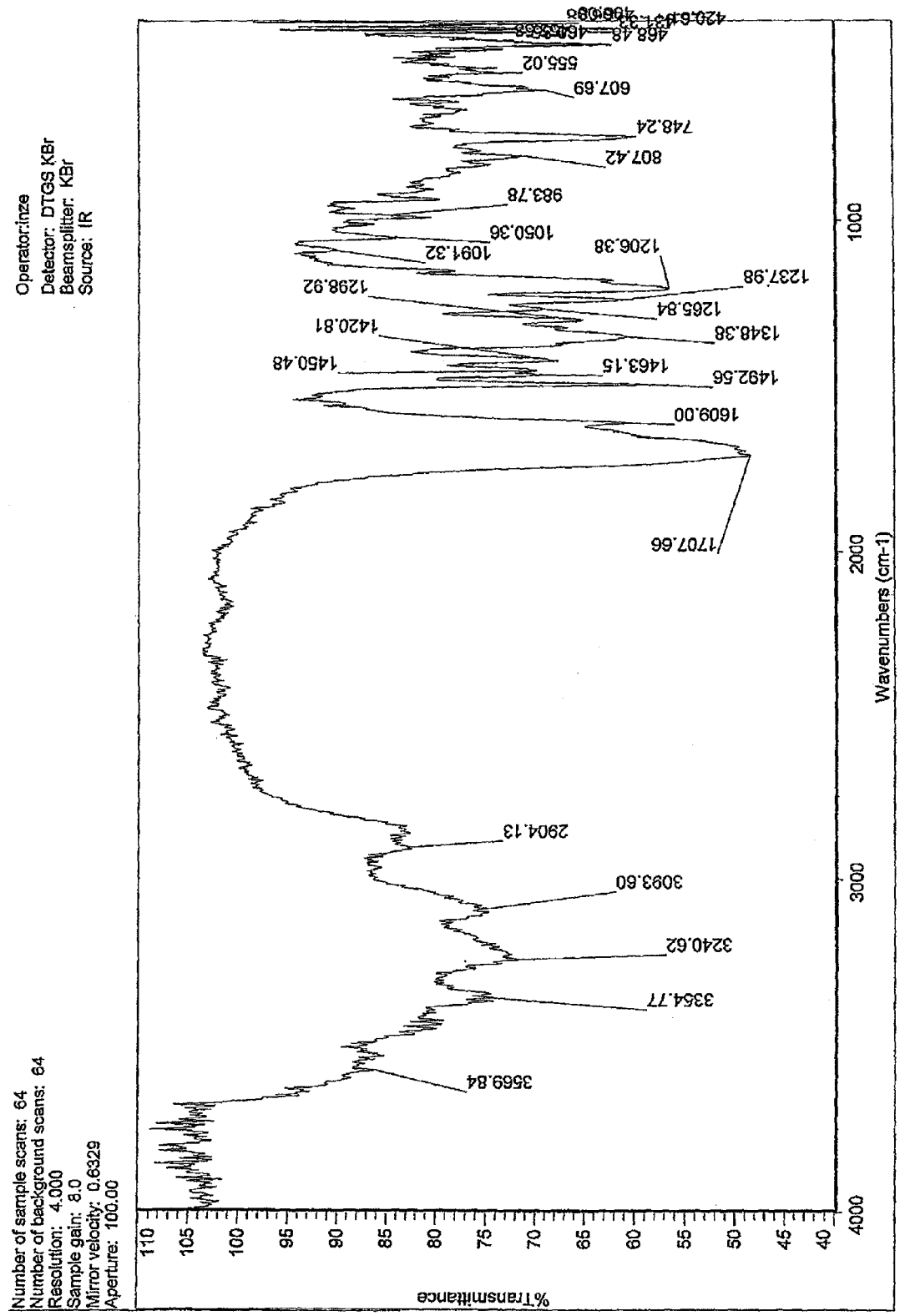

3. The crystalline form of claim 1 having an infrared diffuse-reflectance pattern as substantially shown in FIG. 4a-b.

4. A process for preparing the crystalline form of 3-(4-amino- 1-oxo-1,3-dihydro-isoindol-2-yl)-piperidine-2,6-dione quarterhydrate (1:0.25) of claim 1 comprising:
(a) heating 3-(4-amino-1-oxo-1,3-dihydro-isoindol-2-yl)-piperidine-2,6-dione in an aqueous solution at a concentration of about 10 g/l for about 3 hours at about 60° C.,
(b) isolating the crystalline form of 3-(4-amino-1-oxo-1,3-dihydro-isoindol-2-yl)-piperidine-2,6-dione quarterhydrate from the aqueous solution, and
(c) drying the isolated crystalline form of 3-(4-amino-1-oxo-1,3-dihydro-isoindol-2-yl)-piperidine-2,6-dione quarterhydrate.

5. The crystalline form of claim 1 having an X-ray powder diffraction pattern at approximately 12.1±0.2, 12.6±0.2, 13.4±0.2, 18.9±0.2, 20.0±0.2, 23.9±0.2, 24.7±0.2, 25.8±0.2, and 28.6±0.2 degrees in two theta.

6. A pharmaceutical composition comprising a therapeutically effective amount of the crystalline form of claim 1 and a pharmaceutically acceptable carrier.

7. A process for preparing the crystalline form of 3-(4-amino-1-oxo-1,3-dihydro-isoindol-2-yl)-piperidine-2,6-dione quarterhydrate (1:0.25) of claim 1 comprising:
(a) dissolving 3-(4-amino-1-oxo-1,3-dihydro-isoindol-2-yl)-piperidine-2,6-dione in methanol to produce a first solution,
(b) removing a portion of the methanol from the first solution;
(c) adding water to produce a second mixture;

(d) removing a portion of the water and methanol from the second mixture, then
isolate the crystalline form of 3-(4-amino-1-oxo-1,3-dihydro-isoindol-2-yl)-piperidine-2,6-dione quarterhydrate, and
(e) drying the isolated crystalline form of 3-(4-amino-1-oxo-1,3-dihydro-isoindol-2-yl)-piperidine-2,6-dione quarterhydrate.

* * * * *